(12) United States Patent
Golz-Berner et al.

(10) Patent No.: US 7,829,068 B2
(45) Date of Patent: Nov. 9, 2010

(54) COSMETIC BRONZING AGENT BASED ON DIHYDROXYACETONE

(75) Inventors: Karin Golz-Berner, Monaco (MC); Leonhard Zastrow, Monaco (MC)

(73) Assignee: Coty B.V., Haarlem (DE)

( * ) Notice: Subject to any disclaimer, the term of this patent is extended or adjusted under 35 U.S.C. 154(b) by 366 days.

(21) Appl. No.: 10/570,031

(22) PCT Filed: Sep. 8, 2004

(86) PCT No.: PCT/EP2004/010235

§ 371 (c)(1),
(2), (4) Date: Feb. 28, 2006

(87) PCT Pub. No.: WO2005/025531

PCT Pub. Date: Mar. 24, 2005

(65) Prior Publication Data

US 2007/0009452 A1    Jan. 11, 2007

(30) Foreign Application Priority Data

Sep. 9, 2003    (DE) ................. 103 42 369

(51) Int. Cl.
| | |
|---|---|
| A61K 8/00 | (2006.01) |
| A61K 8/18 | (2006.01) |
| A61K 8/02 | (2006.01) |
| A61K 9/127 | (2006.01) |
| A61K 36/752 | (2006.01) |
| A61K 31/70 | (2006.01) |
| A61Q 17/04 | (2006.01) |
| A01N 65/00 | (2009.01) |
| A01N 43/04 | (2009.01) |

(52) U.S. Cl. .................. 424/59; 424/401; 424/450; 424/736; 514/23

(58) Field of Classification Search ............... 424/59, 424/60, 400, 401, 450
See application file for complete search history.

(56) References Cited

U.S. PATENT DOCUMENTS

| | | | | | |
|---|---|---|---|---|---|
| 2,152,827 | A | * | 4/1939 | Szent-Gyorgyi | 549/403 |
| 5,874,091 | A | * | 2/1999 | Grollier | 424/401 |
| 6,007,796 | A | * | 12/1999 | Menzel et al. | 424/59 |
| 6,623,725 | B2 | * | 9/2003 | Golz-Berner et al. | 424/59 |
| 6,872,401 | B2 | * | 3/2005 | Seyler et al. | 424/401 |
| 6,902,338 | B2 | * | 6/2005 | Puvvada et al. | 401/201 |

FOREIGN PATENT DOCUMENTS

| | | | |
|---|---|---|---|
| WO | WO 8904651 A1 | * | 6/1989 |
| WO | WO 02089770 A2 | * | 11/2002 |

OTHER PUBLICATIONS

Translation of WO/1989/04651.*
Machine translation of WO/2002/089770 A2.*

* cited by examiner

Primary Examiner—Johann R Richter
Assistant Examiner—Luke E Karpinski
(74) Attorney, Agent, or Firm—Novak Druce+Quigg; Greorgy A. Nelson; Gregory M. Lefkowitz

(57) ABSTRACT

A novel cosmetic bronzing agent based on dihydroxyacetone. the bronzing agent contains 0.1-4.5 wt. % dihydroxyacetone (DHA) mounted in a lamellar structure, 0.15-3.5 wt. % free dihydroxyacetone, whereby the ratio between mounted lamellar DHA and free DHA is located in the region of 1:1.5 -1:0.25 and the total amount of DHA is equal to or less than 5 wt, %, also containing 0.01-10 wt % phospholipids and up to 100 wt % cosmetic auxiliary agents, carrier substances, additional active ingredients and mixtures thereof. The bronzing agent has a particularly durable, even and intensive synergistic action.

8 Claims, No Drawings

COSMETIC BRONZING AGENT BASED ON DIHYDROXYACETONE

CROSS REFERENCE TO RELATED APPLICATION

This application is a national stage of PCT/EP2004/010235 filed Sep. 8, 2004 and based upon DE 103 42 369.9 filed Sep. 9, 2003 under the International Convention.

BACKGROUND OF THE INVENTION

1. Field of the Invention

The invention relates to a novel cosmetic tanning agent based on dihydroxyacetone.

2. Description of Related Art

The use of dihydroxyacetone (DHA) as tanning agent for human skin has been known for years. So far, DHA has been combined with various companion substances in order to compensate for the disadvantages which are normally inherent in this product. It is known to produce self-tanning agents based on dihydroxyacetone (DHA) in the form of various liquid emulsions or gels. In many cases, however, these must contain further additives in order to be stable. In WO96/31190, combinations of DHA with lecithins and optionally sterols are heated in an aqueous solution and then encapsulated in liposomes in order to stabilize them. In addition, WO 01/70186 describes a cosmetic powder containing DHA, a mahakanni extract and a tulip extract.

EP 954277 discloses a cosmetic self-tanning agent which, in addition to certain UV filters, contains DHA encapsulated in liposomes and free DHA and is intended to achieve a natural tan of the skin.

SUMMARY OF THE INVENTION

The object of the invention is to provide a cosmetic tanning agent which has a very even, intensive and long lasting tanning effect.

The novel cosmetic tanning agent contains 0.1 to 4.5 wt. % dihydroxyacetone (DHA) incorporated in a lamellar structure and 0.15 to 3.5 wt. % free dihydroxyacetone, the ratio of DHA incorporated in lamellae and free DHA ranging between 1:1.5 and 1:0.25, 0.01 to 10 wt. % phospholipids, and cosmetic auxiliary agents, carrier substances, additional active ingredients and mixtures thereof up to 100 wt. %, all percentages being relative to the tanning agent's total weight.

Preferably, said agent contains 0.1 to 1.5 wt. % DHA incorporated in a lamellar structure and 0.15 to 2.5 wt. % free DHA.

The DHA incorporated in lamellae can be a product which is processed together with phospholipids, such as phosphatidylcholine, which are able to form such a lamellar structure. In doing so, additional auxiliary agents can be used, such as water, alcohols, e.g. glycerine, pentylene glycol, and oils, such as e.g. Neutral Oil, Shea butter, Squalane or Ceramid III.

Said lamellar structure is achieved by means of a special high-pressure homogenization process, wherein DHA is incorporated into the lamellae in a very finely distributed manner. This production procedure using phospholipids, alcohol, lipids and water which are heated is known e.g. from WO02/089770, Examples 1-3.

The combination of DHA particles incorporated in lamellae and free DHA particles does not only enhance the achieved tan to a certain expectable extent, but also brings about a long-term effect. Long-term effect means that the tan lasts for at least 5 days, preferably at least 7 days, following a single application.

In contrast to DHA encapsulated in liposomes as in EP 954277, the long lasting effect is enhanced instead of improving the skin's natural look after tanning.

Phospholipids which can be used include e.g. phosphatidylcholine, phosphatidyl ethanolamine, phosphatidyl inositol, phosphatidyl serine, phosphatidic acid, lysolecithins and sphingolipids as well as mixtures thereof. A known product is e.g. Phospholipon®.

The novel tanning agent can additionally contain an alcoholic extract from orange peels in an amount ranging between 0.01 and 5 wt. %. Said extract is preferably obtained using propylene glycol as extractant at a temperature of max. 40° C.

Moreover, the novel tanning agent can additionally contain an alcoholic extract from tulips in an amount ranging between 0.5 and 10 wt. %. Said extract is preferably obtained using propylene glycol as extractant as well, at a temperature of max. 60° C.

It is advantageous that the aforesaid extracts be added in dried form, i.e. the above percentages of orange and tulip are based on the dry weight of the respective extract relative to the agent's total weight.

In another embodiment of the invention, a liquorice extract can be added to the inventive agent in an amount ranging between 0.001 and 1 wt. %.

The inventive agent further contains cosmetic auxiliary agents and carrier substances as they are commonly used in such preparations, e.g. water, preservatives, colourants, pigments having a colouring effect, thickeners, fragrances, alcohols, polyols, esters, electrolytes, gel-forming agents, polar and non-polar oils, polymers, copolymers, emulsifiers, waxes, stabilizers, wherein the presence of emulsifiers, preservatives, paraffin and colourants is avoided if possible, i.e. formulations without the last-mentioned substances are preferred.

The inventive agent can be provided as a gel or an emulsion or a gel emulsion. For this purpose, usual gel-forming agents or emulsifiers can be used.

Additional active ingredients can be e.g. inorganic and organic sunscreens, free radical scavengers, moisturizers, vitamins, enzymes, plant-based active agents, polymers, melanin, antioxidants, anti-inflammatory natural active agents, asymmetric lamellar aggregates loaded with oxygen according to WO 94/00109; products obtained by the gentle ultrasonic decomposition of yeasts or vegetable matter according to WO 94/13783; kaolin and kaolin which has been modified with $SiO_2$ according to WO94/17588.

Another preferred embodiment of the invention consists in that an active preparation with a high radical protection factor is added to the tanning agent, which preparation consists of the following ingredients: a product obtained by extracting the bark of Quebracho blanco and subsequent enzymatic hydrolysis, which product contains at least 90 wt. % proanthocyanidine oligomers and max. 10 wt. % gallic acid, in microcapsules, and a silkworm extract obtained by extraction, which extract contains the peptide cecropine, amino acids and a vitamin mixture, and a non-ionic, cationic or anionic hydrogel or hydrogel mixture, and one or several phospholipid(s), and water according to WO99/66881, e.g. an active complex according to Example 1 or 2, or according to WO 01/26617, e.g. an active complex according to the example with further additives.

In addition, emollients or moisturizers or mixtures thereof can also be contained.

A large number of compounds can normally be used as emollients, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, isopropyl myristate, isopropyl palmitate, oleyl alcohol, isopropyl laurate, decyl oleate, octadecane-2-ol, isocetyl alcohol, cetyl palmitate, silicone oils such as dimethylpolysiloxane, polyethylene glycol, lanolin, cocoa butter, vegetable oils such as maize oil, cotton seed oil, olive oil, mineral oils, butyl myristate, palmitic acid, etc.

Preferred moisturizers are glycerine, butylene glycol, propylene glycol and mixtures thereof.

Antioxidants include vitamins such as vitamin C and derivatives thereof, e.g. ascorbyl acetate, ascorbyl phosphate and ascorbyl palmitate; vitamin A and derivatives thereof; folic acid and derivatives thereof; vitamin E and derivatives thereof such as tocopheryl acetate; flavons or flavonoids; amino acids such as histidine, glycine, tyrosine, tryptophan and derivatives thereof; carotenoids and carotenes such as e.g. α-carotene, β-carotene; uric acid and derivatives thereof; α-hydroxy acids such as citric acid, lactic acid, malic acid; stilbenes and derivatives thereof; and pomegranate extracts.

Advantageously, the inventive compositions further contain suitable water- and/or oil-soluble UVA or UVB filters or both. Advantageous oil-soluble UVB filters include derivatives of 4-aminobenzoic acid such as 4-(dimethylamino)-benzoic acid-(2-ethylhexyl) ester; esters of cinnamic acid such as 4-methoxy cinnamic acid(2-ethylhexyl) ester; benzophenone derivatives such as 2-hydroxy-4-methoxy benzophenone; derivatives of 3-benzylidene camphor such as 3-benzylidene camphor.

Preferred oil-soluble UV filters are Benzophenone-3, Butyl methoxybenzoylmethane, Octyl Methoxycinnamate, Octyl Salicylate, 4-Methylbenzylidene Camphor, Homosalate and Octyl Dimethyl PABA.

Water-soluble UVB filters are e.g. sulphonic acid derivatives of benzophenone or of 3-benzylidene camphor, or salts such as the Na salt or K salt of 2-phenylbenzimidazol-5-sulphonic acid.

UVA filters include derivatives of dibenzoylmethane such as 1-phenyl-4-(4'-iso-propylphenyl)propane-1,3-dione.

The inventive cosmetic compositions can e.g. be used in the form of suncreams, sun gels, after-sun products, pre-sun products, day creams, night creams, masks, body lotions, body powder, eye cosmetics, and in decorative cosmetic products such as lipsticks, gels, eyeshadows, compact powder or compact wax, rouge, foundation, make-up, etc. The aforesaid products are manufactured in a way known to those skilled in the art.

The novel cosmetic tanning composition has an effect which exceeds expectations as regards the extent of a longer lasting tan due to the incorporation of DHA in the lamellar phospholipid structure. Compared to DHA incorporated in a liposomal structure, the tanning effect lasts nearly twice as long. In addition, a very even tan is achieved whose intensity reduces only slowly.

Moreover, the presence of orange peel extract makes the tan look particularly natural. The tan's intensity can be enhanced by adding the aforedescribed tulip extract, which is preferably obtained from garden and wild tulips of the Tulipa family.

Comparative tests were carried out, which show a synergistic effect of free DHA and DHA enclosed in lamellae as well as of DHA combined with orange peel extract compared to the individual components.

DETAILED DESCRIPTION OF THE INVENTION

The invention will now be explained in more detail by means of examples. All quantities are in weight per cent unless indicated otherwise.

Example 1

Self-Tanning Cream I

| Phase A | |
|---|---|
| Water | q.s. ad 100 |
| Glycerine | 2.0 |
| Propylene Glycol | 2.0 |
| Phase B | |
| Cetearyl Alcohol | 2.6 |
| Steareth-2 | 2.0 |
| Steareth-21 | 1.6 |
| $C_{12-15}$ Alkyl Benzoate | 2.1 |
| Dicaprylyl Carbonate | 2.0 |
| Phase C | |
| Dihydroxyacetone | 2.0 |
| Dihydroxyacetone in lamellae* | 5.0 |
| Tulip extract (spray-dried) | 1.0 |

*Consisting of 30% DHA, 6% phosphatidylcholine, 10% lipids, 8% solvent and 46% water (wt. %).

Phases A and B were prepared separately, combined with one another at approx. 65° C., homogenized for approx. 10 minutes, and cooled down to 35° C. while stirring. Then, Phase C was stirred in at approx. 25° C. The pH value was adjusted to 4.5.

Example 2

Self-Tanning Gel for Body and Face

| Phase A | |
|---|---|
| Water | q.s. ad 100 |
| Glycerine | 3.5 |
| Carbomer | 1.8 |
| Propylene Glycol | 3.5 |
| Phase B | |
| Dihydroxyacetone | 1.0 |
| Dihydroxyacetone in lamellae* | 10.0 |
| Tulip extract (spray-dried) | 2.0 |
| Orange extract (spray-dried) | 1.5 |
| Phase C | |
| Perfume Oil | 0.5 |
| Preservative | 0.5 |

*Consisting of 30% DHA, 6% phosphatidylcholine, 10% lipids, 8% solvent and 46% water (wt. %).

Phase A was heated up to 40° C. while stirring. Phase B, which had been prepared separately, was stirred in at the aforesaid temperature. Then, Phase C was stirred in, and the pH value was adjusted to 4.5.

Example 3

Self-Tanning Cream II

| Phase A | |
| --- | --- |
| Water | q.s. ad 100 |
| Glycerine | 2.0 |
| Propylene Glycol | 2.0 |
| Phase B | |
| Cetearyl Alcohol | 2.6 |
| Steareth-2 | 2.0 |
| Steareth-21 | 1.6 |
| $C_{12-15}$ Alkyl Benzoate | 2.1 |
| Dicaprylyl Carbonate | 2.0 |
| Phase C | |
| Dihydroxyacetone | 1.5 |
| Dihydroxyacetone in lamellae* | 2.1 |
| Tulip extract (spray-dried) | 1.0 |

*Consisting of 30% DHA, 6% phosphatidylcholine, 10% lipids, 8% solvent and 46% water (wt. %).

Processing is done as in Example 1.

Example 4

Self-Tanning Cream III

| Phase A | |
| --- | --- |
| Water | q.s. ad 100 |
| Glycerine | 2.5 |
| Propylene Glycol | 1.9 |
| Phase B | |
| Cetearyl Alcohol | 2.6 |
| Steareth-2 | 2.0 |
| Steareth-2 1 | 1.6 |
| $C_{12-15}$ Alkyl Benzoate | 2.1 |
| Dicaprylyl Carbonate | 2.0 |
| Phase C | |
| Dihydroxyacetone | 4.2 |
| Dihydroxyacetone in lamellae* | 2.8 |
| Tulip extract (spray-dried) | 0.8 |

*Consisting of 30% DHA, 6% phosphatidylcholine, 10% lipids, 8% solvent and 46% water (wt.%).

Processing is done as in Example 1.

Example 5

Comparative Test

In a group of 12 test persons with normal-to-dry skin, two areas measuring 2 cm² each were marked on the forearm of each test person, and two different self-tanning creams were applied thereto. Cream A was equivalent to the composition of Example 1. Cream B did not contain 5% DHA in lamellae, but the same amount of DHA encapsulated in liposomes instead.

Immediately after the cream had been applied, each tester compared the shade achieved with a colour scale. Said colour scale showed brown tones from 1 to 10, 10 representing the darkest brown tone. The measurements are shown in Table 1. During the test period, the test persons' forearms were always covered and not exposed to UV radiation.

The results in Table 1 show a reduction of the brown tone's intensity from the mean value of 8.6 to 4.4 for Cream B, while the value for Cream A only reduced from 8.6 to 7.7.

TABLE 1

| | Skin shade achieved according to scale 1-10 | | | | | | | |
| --- | --- | --- | --- | --- | --- | --- | --- | --- |
| Test | Start | | after 24 h | | after 3 days | | after 7 days | |
| persons | A | B | A | B | A | B | A | B |
| 1 | 9 | 9 | 9 | 8 | 8 | 6 | 8 | 4.5 |
| 2 | 8 | 8 | 8 | 7 | 7 | 5 | 7 | 4 |
| 3 | 9 | 8 | 9 | 8 | 8 | 6 | 7.5 | 5 |
| 4 | 9 | 9 | 9 | 8 | 9 | 7 | 8 | 5 |
| 5 | 9 | 9 | 8 | 8 | 8 | 6 | 8 | 5 |
| 6 | 8 | 9 | 8 | 8 | 8 | 7 | 7 | 4 |
| 7 | 9 | 9 | 9 | 7 | 8 | 5.5 | 8 | 4.5 |
| 8 | 9 | 8 | 8 | 8 | 8 | 6 | 8 | 4 |
| 9 | 9 | 9 | 8 | 7 | 7 | 5 | 7 | 3.5 |
| 10 | 9 | 9 | 9 | 8 | 9 | 7 | 8 | 5 |
| 11 | 9 | 9 | 8 | 7 | 8 | 6 | 8 | 4 |
| 12 | 9 | 8 | 8 | 8 | 8 | 6 | 8 | 4.5 |
| Ø | 8.8 | 8.6 | 8.4 | 7.7 | 8.0 | 6.0 | 7.7 | 4.4 |

The invention claimed is:

1. A cosmetic tanning agent based on dihydroxyacetone comprising 0.1 to 4.5 wt. % dihydroxyacetone (DHA) incorporated in lamellae resulting from a mixture of phospholipids, lipids, organic solvents, water and DHA and prepared by a high-pressure homogenization process, 0.15 to 3.5 wt. % free dihydroxyacetone, the ratio of DHA incorporated in lamellae and free DHA ranging between 1:1.5 and 1:0.25 and the total amount of DHA contained being equal to or less than 5 wt. %, 0.01 to 10 wt. % phospholipids, 0.01 to 5 wt. % of an alcoholic extract from orange peels, 0.5 to 8 wt. % of an alcoholic extract from tulips, and cosmetic auxiliary agents, carrier substances, additional active ingredients and mixtures thereof up to 100 wt. %, all percentages being relative to the tanning agent's total weight.

2. A tanning agent according to claim 1, wherein said mixture of phospholipids, lipids, organic solvents, water and DHA contains DHA in an amount of 4 to 12 wt. %.

3. A tanning agent according to claim 1, wherein said agent contains 1 to 4.0 wt. % dihydroxyacetone (DHA) incorporated in lamellae.

4. A tanning agent according to claim 1, wherein said agent contains 0.5 to 2.0 wt. % free dihydroxyacetone.

5. A tanning agent according to claim 1, wherein said agent contains 0.1 to 1.5 wt. % DHA incorporated in lamellae and 0.15 to 2.5 wt. % free DHA.

6. A tanning agent according to claim 1, wherein said agent additionally contains a liquorice extract in an amount ranging between 0.001 and 1 wt. %.

7. A cosmetic tanning agent based on dihydroxyacetone comprising 0.1 to 4.5 wt. % dihydroxyacetone (DHA) incorporated in lamellae prepared by a high-pressure homogenization process, 0.15 to 3.5 wt. % free dihydroxyacetone, the ratio of DHA incorporated in lamellae and free DHA ranging between 1:1.5 and 1:0.25 and the total amount of DHA contained being equal to or less than 5 wt. %,
0.01 to 10 wt. % phospholipids,
0.01 to 5 wt. % of an alcoholic extract from orange peels,
0.5 to 8 wt. % of an alcoholic extract from tulips, and
cosmetic auxiliary agents, carrier substances, additional active ingredients and mixtures thereof up to 100 wt. %, all percentages being relative to the tanning agent's total weight.

8. The cosmetic tanning agent of claim 1, wherein the alcoholic extract from orange peels is obtained with propylene glycol at a maximum temperature of 40° C.

* * * * *